US011541109B2

(12) United States Patent
Seo et al.

(10) Patent No.: US 11,541,109 B2
(45) Date of Patent: Jan. 3, 2023

(54) METHOD FOR PREPARING LIVE ATTENUATED VACCINE BY IRRADIATION AND LIVE ATTENUATED VACCINE COMPOSITION PREPARED BY THE SAME (71) Applicant: KOREA ATOMIC ENERGY RESEARCH INSTITUTE, Daejeon (KR)

(72) Inventors: Ho-Seong Seo, Jeongeup-si (KR); Sang-Yong Lim, Daejeon (KR); Jong-Hyun Jung, Seoul (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 16/955,735

(22) PCT Filed: Jan. 8, 2019

(86) PCT No.: PCT/KR2019/000298
§ 371 (c)(1),
(2) Date: Jun. 18, 2020

(87) PCT Pub. No.: WO2020/145426
PCT Pub. Date: Jul. 16, 2020

(65) Prior Publication Data
US 2021/0369829 A1 Dec. 2, 2021

(51) Int. Cl.
| | |
|---|---|
| *A61K 39/112* | (2006.01) |
| *A61K 39/02* | (2006.01) |
| *A61K 39/00* | (2006.01) |
| *A61K 41/17* | (2020.01) |
| *A61K 39/108* | (2006.01) |
| *A61K 39/04* | (2006.01) |
| *A61K 39/085* | (2006.01) |
| *A61K 39/09* | (2006.01) |
| *A61K 39/095* | (2006.01) |

(52) U.S. Cl.
CPC ........ *A61K 39/025* (2013.01); *A61K 39/0258* (2013.01); *A61K 39/0275* (2013.01); *A61K 39/04* (2013.01); *A61K 39/085* (2013.01); *A61K 39/092* (2013.01); *A61K 39/095* (2013.01); *A61K 39/099* (2013.01); *A61K 39/107* (2013.01); *A61K 41/17* (2020.01); *A61K 2039/522* (2013.01)

(58) Field of Classification Search
None
See application file for complete search history.

(56) References Cited

U.S. PATENT DOCUMENTS

| | | | |
|---|---|---|---|
| 2014/0037700 A1 | 2/2014 | Fisher | |
| 2014/0206016 A1* | 7/2014 | Lozano Sanchez | ... C12Q 1/045 435/7.1 |
| 2016/0089430 A1 | 3/2016 | Bronshtein | |
| 2017/0121701 A1 | 5/2017 | Dobrinsky et al. | |

FOREIGN PATENT DOCUMENTS

| | | |
|---|---|---|
| CN | 105833259 A | 8/2016 |
| GB | 902760 A | 8/1962 |
| KR | 10-2011-0053345 A | 5/2011 |
| KR | 10-2014-0053887 A | 5/2014 |
| KR | 10-2016-0062289 A | 6/2016 |
| KR | 10-2019-0004564 A | 1/2019 |
| WO | 2010012045 A1 | 2/2010 |
| WO | 2016149771 A1 | 9/2016 |

OTHER PUBLICATIONS

Borai et al. Med. J. Cairo Univ. 86: 1193-1202, Jun. 2018.*
Sarjeant et al. Poultry Sci. 84: 955-958, 2005.*
Choi et al. KR 2013105975 A—English Abstract.*
[Exclusive] Solve 'the Ineffective Vaccine' Problem and Develop New Radiation-Based Vaccine Manufacturing Technology(URL: http://news1.kr/articles/2915010) and extract translation from lines 3 on p. 2 to lines 23 on p. 2 2017.
"[Interview] Securing Source Technology for Vaccine Development Using Radiation" (URL: http://news1.kr/articles/2916830) and extract translation from lines 2 on p. 2 to lines 10 on p. 3 2017.
Ahmed Ammar et al., "Evaluation of irradiated vaccine prepared from *Salmonella typhimurium* isolated from buffalo calves". International Journal of Research in Pure and Applied Microbiology, 2014, vol. 4, pp. 10-14.
Ho Seong Seo, "Application of radiation technology in vaccines development", Clinical and Experimental Vaccine Research, 2015, vol. 4, pp. 145-158.
Alsharifi et al. (Feb. 1, 2010) "The Gamma-Irradiated Influenza Vaccine and the Prospect of Producing Safe Vaccines in General", Immunology And Cell Biology, 88(2):103-104.
Gaidamakova et al. (May 14, 2012) "Preserving Immunogenicity of Lethally Irradiated Viral and Bacterial Vaccine Epitopes Using a Radio-Protective Mn2+ -Peptide Complex from Deinococcus", Cell Host & Microbe, 12(1):117-124.
Eitner et al. (Jan. 1, 2017) "Using Electrons to Inactivate Viruses", Research News, 3 pages.
Jesudhasan et al. (2015) "Electron-Beam-Inactivated Vaccine Against *Salmonella enteritidis* Colonization in Molting Hens", Avian Diseasess, 59(1):165-170.

(Continued)

*Primary Examiner* — S. Devi
(74) *Attorney, Agent, or Firm* — Fox Rothschild LLP (57) ABSTRACT

The present invention relates to a method of preparing a live attenuated vaccine by irradiation and a live attenuated vaccine composition prepared by the same, and more particularly, a method of preparing a live attenuated vaccine by irradiation including irradiating a pathogenic microorganism with a dose of 0.5 to 2 kGy of radiation per single radiation six to fifteen times; and a live attenuated vaccine composition including a pathogenic microorganism attenuated to not be revertant to a wild type by generation of at least one mutation of nucleotide insertion and nucleotide deletion by irradiation.

6 Claims, 7 Drawing Sheets

(56) References Cited

OTHER PUBLICATIONS

Thabet et al. (2019) "Eimeria Tenellaoocysts Attenuated by Low Energy Electron Irradiation (LEEI) Induce Protection Against Challenge Infection in Chickens", Veterinary Parasitology, 266:18-26.
Li et al. (Feb. 16, 2016) "X-ray Irradiated Vaccine Confers Protection Against Pneumonia Caused by Pseudomonas Aeruginosa", Scientific Reports, 6(1):1-12.
Extended European Search Report for Application No. EP 19886054.6, dated Mar. 11, 2022, 19 pages.
Office action dated Sep. 15, 2022 in Chinese Application No. 201980006484.10.

\* cited by examiner

METHOD FOR PREPARING LIVE ATTENUATED VACCINE BY IRRADIATION AND LIVE ATTENUATED VACCINE COMPOSITION PREPARED BY THE SAME

This application is the national stage of International Application PCT/KR2019/000298 filed 8 Jan. 2019, the entire contents of which are incorporated herein by reference.

TECHNICAL FIELD

The present disclosure relates to a method for preparing a live attenuated vaccine by irradiation and a live attenuated vaccine composition prepared by the same, and more particularly, a method for preparing a non-invasive live attenuated vaccine using irradiation and a vaccine composition prepared by the same.

BACKGROUND ART

A method of a warm-blooded animal to overcome a cause of disease from microorganisms may be a complex process. Immunity to a cause of disease from microorganisms may be obtained by making a warm-blooded animal to weakly express a pathogenic state in advance.

Generally, a vaccine including live and attenuated microorganisms as a main component may be referred to as an attenuated vaccine, a live vaccine, or the like, and it is known that such vaccines may induce a highly effective immune reaction as compared to a an inactivated vaccine. When microorganism pathogens are introduced into an animal host after the host is vaccinated, such vaccines may control additional replication of organisms by accelerating recovery of early immunity, cell-mediated immunity, or humoral immunity, before a clinically significant infection rate is exhibited. A vaccine including inactivated pathogens as a main component, an inactivated vaccine, may not be able to induce the above-described type of reaction.

However, there may be a problem in which a vaccine including live attenuated pathogens may not remove a risk that a vaccinated host may contract a disease that the host tries to prevent at the time of vaccination, depending on a degree of attenuation of a live vaccine. Thus, it is necessary to develop a vaccine having immunization properties and which may not cause undesirable side effects at the time of vaccination, and almost no possibility of substantial revertant of live attenuated vaccine strains to toxigenic wild-type strains should be present.

As a general method for preparing a live attenuated vaccine, a method of subculturing a pathogenic microorganism for an extended period of time to attenuate or remove toxicity of the pathogenic microorganism by a natural mutation method, a method of using a toxic chemical substance or ultraviolet (UV) rays as a mutagen to increase a mutation rate by an artificial mutation method, and the like, may be used. The former may be based on spontaneous DNA mutation, and it may take at least one hundreds sequential culture which takes a relatively long time, to isolate attenuated vaccine strains, while the latter may shorten the time for development as compared to natural mutation. However, most of general methods for preparing a live attenuated vaccine may mostly induce point mutation by base substitution such that, when the mutated base is back-mutated, pathogenicity may be resumed and an attenuated vaccine may change to a pathogenic strain, a revertant, which may be a problem. An incident in which *Brucella* vaccine strains distributed in 1998 were revertant to highly dangerous pathogens and 20,000 head of cattle were killed is an example of the above-described problem in South Korea.

Preparation method of a vaccine using irradiation has been applied to preparation of an inactivated vaccine in which microorganisms are inactivated as disclosed in US2016-0089430 A1, but a technique of preparing a live attenuated vaccine using the same has not been developed. If it is possible to secure a large amount of attenuated stains using irradiation in a short period of time, it is expected that the technique may contribute to shortening the time for development of an attenuated vaccine and reduce the possibility of mutation revertant.

A1, but a technique of preparing a live attenuated vaccine using the same has not been developed. If it is possible to secure a large amount of attenuated stains using irradiation in a short period of time, it is expected that the technique may contribute to shortening the time for development of an attenuated vaccine and reduce the possibility of mutation revertant.

SUMMARY OF THE INVENTION

An aspect of the present disclosure is to provide a method for securing a large amount of attenuated strains for a short period of time.

Another aspect of the present disclosure is to provide attenuated strains which may not be revertant to wild stains.

According to an aspect of the present disclosure, a method for preparing a live attenuated vaccine by irradiation is provided, the method including irradiating a pathogenic microorganism with a dose of 0.5 to 2 kGy of radiation per single radiation six to fifteen times.

According to another aspect of the present disclosure, a live attenuated vaccine composition is provided, the live attenuated vaccine composition including a pathogenic microorganism attenuated to not be revertant to a wild type by generation of at least one mutation of nucleotide insertion and nucleotide deletion by irradiation.

According to the present disclosure, a large amount of safe live attenuated vaccine which may address the issue of revertancy by inducing nucleotide insertion and nucleotide deletion, which may not be generated in a general method of inducing mutation, through repeated irradiation may be secured within a short period of time such that a period of development of an attenuated vaccine may be shortened.

BRIEF DESCRIPTION OF DRAWINGS

FIG. 1(*a*) is a graph illustrating invasion into an animal cell depending on the number of irradiations and FIG. 1(*b*) is a graph illustrating intracellular replication depending on the number of irradiations;

FIG. 2(*a*) illustrates an infection rate of macrophages depending on the dose of radiation, and FIG. 2(*b*) illustrates a degree of dead cells of *salmonella* depending on the dose of radiation;

DETAILED DESCRIPTION

Hereinafter, example embodiments of the present disclosure will be described with reference to the accompanying drawings. Example embodiments of the present disclosure, however, may be modified in various manners, and a scope of the present disclosure may not be limited to the example embodiments described below.

According to the present disclosure, a method for preparing a non-invasive live attenuated vaccine using irradiation and a live attenuated vaccine composition prepared by the same may be provided.

More particularly, the method for preparing a live attenuated vaccine using irradiation may include irradiating a pathogenic microorganism with a dose of 0.5 to 2 kGy of radiation six to fifteen times, and preferably, dose of 0.5 kGy or higher and less than 2 kGy of radiation, does of 1 kGy to 1.5 kGy radiation, for example, may be applied, and more preferably, does of 1 kGy of radiation approximately may be applied.

When dose of radiation per single radiation is less than 0.5 kGy, sufficient mutation may not be formed such that attenuation may not be obtained, whereas, when dose of radiation per single radiation exceeds 2 kGy, a pathogenic microorganism may become dead cells such that a live attenuated vaccine may not be obtained.

The method for preparing a live attenuated vaccine by irradiation may include irradiating a pathogenic microorganism with a dose of 0.5 to 2 kGy radiation; and culturing the irradiated pathogenic microorganism, and the irradiating and the culturing maybe repeated six to fifteen times.

In the present disclosure, the irradiation may be performed six to fifteen times, and the radiation maybe applied ten to twelve times preferably. When the number of irradiations is less than six times, invasion of pathogens into cells may not sufficiently decrease as indicated in FIG. 1(a) such that it maybe insufficient to secure stability. When the number of irradiations exceeds fifteen times, growth maybe inhibited due to mutation such that it may not be possible to use the pathogenic microorganism as a vaccine strain.

The pathogenic microorganism to which the present disclosure may be applied may be selected from among a group consisting of *Escherichia* genus, *Salmonella* genus, *Vibrio* genus, *Streptococcus* genus, *Bordetella* genus, Mycobacteria genus and *Staphylococcus* genus. For example, it may be preferable to replicate the pathogenic microorganism to which the present disclosure may be applied by invasion into eukaryotes. The example of the pathogenic microorganism may include *Salmonella* genus, *Bordetella* genus, *Vibrio* genus, Mycobacteria genus, *Haemophilus* genus, *Escherichia* genus, and the like.

Specifically, the pathogenic microorganism may be *S. typhi, S. typhimurium, S. enteritidis, S. choleraesuis*, Bor-*detella pertussis, Haemophilus influenza, Neisseria gonorrhoeae, Escherichia coli, Streptococcus pneumoniae, Staphylococcus aureus*, and the like.

Preferably, the pathogenic microorganism may be *Salmonella typhimurium, Salmonella gallinarum, Streptococcus pneumoniae*, or *Staphylococcus aureus*. For example, the pathogenic microorganism may be *Salmonella typhimurium* KST0569 (KCTC13193BP).

*Salmonella typhimurium* KST0569 (KCTC13193BP) strain was deposited in KCTC (Korean Collection for Type Cultures) by a deposit No. of KCTC 13193BP.

In the process of alternatively performing the irradiating and the culturing the irradiated pathogenic microorganism, the culturing the irradiated pathogenic microorganism may be performed for six to forty-eight hours, and preferably, the culturing may be performed for twelve to twenty-four hours. When the culturing is performed for less than six hours, revertant of a cell DNA change by irradiation may be incomplete such that there may be a problem in growth. When the culturing is performed for more than forty-eight hours, there may be a problem of autolysis.

The culturing may be performed under conditions appropriate for culturing of a pathogenic microorganism, and may not be limited to any particular conditions. The culturing may be performed under conditions considered appropriate, including and using an appropriate culture, along with nutrient components of the pathogenic microorganism.

For example, a nutrient culture used to culture *Salmonella typhimurium* may be cultured under conditions of 37° C. and 180 rpm with low sodium LB (Bacto-trypton 10 g/L, Bacto-yeast extract 5 g/L, NaCl 5 g/L).

According to another aspect of the present disclosure, a live attenuated vaccine composition including a pathogenic microorganism attenuated to not be revertant to a wild type by at least one mutation of nucleotide insertion and nucleotide deletion may be provided, and a method of irradiation applied thereto may be the same as in the descriptions of the method of preparing a live attenuated vaccine by irradiation described above.

Thus, the irradiation may be performed by applying dose of 0.5 to 2 kGy of radiation six to fifteen times. For example, the irradiating and the culturing the irradiated pathogenic microorganism described above may be alternatively performed six to fifteen times.

The pathogenic microorganism to which the present disclosure is applied may be selected from among a group consisting of *Escherichia* genus, *Salmonella* genus, *Vibrio* genus, *Streptococcus* genus, *Bordetella* genus, Mycobacteria genus and *Staphylococcus* genus. For example, it may be preferable to replicate the pathogenic microorganism to which the present disclosure may be applied by invasion into eukaryotes. As an example of the pathogenic microorganism, there may be *Salmonella* genus, *Bordetella* genus, *Vibrio* genus, *Haemophilus* genus, *Escherichia* genus, and the like.

Specifically, the pathogenic microorganism may be *S. typhi, S. typhimurium, S. enteritidis, S. Choleraesuis*, Bor-*detella pertussis, Haemophilus influenza, Neisseria gonorrhoeae, Escherichia coli, Streptococcus pneumoniae, Staphylococcus aureus*, or the like.

Preferably, the pathogenic microorganism may be *Salmonella typhimurium, Salmonella gallinarum, Streptococcus pneumoniae*, or *Staphylococcus aureus*. For example, the pathogenic microorganism maybe *Salmonella typhimurium* KST0569 (KCTC 13193BP).

The live attenuated vaccine composition of the present disclosure may be used to prevent any disease caused by the above-mentioned pathogenic microorganisms. For example, the live attenuated vaccine composition may be used for preventing typhoid, *salmonellosis*, food poisoning, pertussis, meningitis, gonorrhea, and the like, and may be used for preventing a *salmonellosis* disease including a septicemic type exhibiting a symptom similar to typhoid, and acute gastroenteritis *salmonellosis*, food poisoning.

The live attenuated vaccine composition may be used for preventing diseases derived from *Streptococcus pneumoniae* or *Staphylococcus aureus*. More specifically, the live attenuated vaccine composition may be used for preventing diseases derived from *Streptococcus pneumoniae*, causing acute purulent diseases such as meningitis, septicemia, empyema, and peritonitis or may be used for preventing various infectious diseases including staphylococcal scalded skin syndrome, staphylococcal food poisoning, toxic shock syndrome, diseases derived from *Staphylococcus aureus* such as skin infectious diseases, endocarditis, pneumonia, empyema, osteomyelitis, infectious arthritis, spinal osteomyelitis, and the like.

When a host (particularly a human host) is administrated with an effective dosage of the vaccine described in the present disclosure, the host may be preemptively treated with respect to infection caused by microorganisms. A dose of vaccine used in such a treatment method may be dependent upon various clinical factors including a height and a weight of a host and a form of a prepared vaccine. For example, in the case of *Salmonella typhimurium* KST0569 (KCTC13193BP), generally, a dose containing $10^9$ to $10^{11}$ of organisms per dosage may be administrated to an adult host with a weight of 70 kg.

Also, according to the present disclosure, a pharmaceutical composition for treating or preventing relevant diseases including live attenuated bacteria prepared by the above-described method may be provided.

The vaccine composition and the pharmaceutical composition for treating or preventing disease in the present disclosure may include a pharmaceutically acceptable carrier or excipient in addition to live attenuated bacteria obtained by the present disclosure. The live attenuated bacteria of the present disclosure may be included in effective concentration.

In the example embodiment, the terms "effective concentration" or "containing as an active ingredient or an effective component" may indicate a content of live attenuated bacteria that may be sufficient to obtain a desired effect, to generate an enough antibody for inducing desired immune reaction when the live attenuated bacteria is invaded into a host cell, as compared to a state in which the live attenuated bacteria is significant less invaded.

In detail, the effective concentration in the example embodiment may be varied in accordance with an age, a sex, and a weight of a patient, and may be increased in accordance with an administration route, a sex, a weight, an age, and the like. Thus, the dosage may not limit a scope of the present disclosure in anyway.

In the example embodiment, the term "pharmaceutically acceptable carrier" may refer to various carriers used in the related art. A generally used transportation system for selecting a pharmaceutical carrier may be used. A medicine transport system may include a solution, a suspension gel, a microsphere, a polymer substance such as solubility-denaturalization substances (ethanol, propylene glycol, sucrose), a polymer (polycaprolactone, PLGA), and the like.

As the pharmaceutically acceptable carrier contained in the pharmaceutical composition in the example embodiment, a generally used substance may be used.

For example, the pharmaceutically acceptable carrier may include lactose, dextrose, sucrose, solbitol, mannitol, starch, acacia rubber, calcium phosphate, arginate, gelatin, calcium silicate, microcrystal line cellulose, polyvinylpyrrolidone, cellulose, water, syrup, methylcellulose, methyl hydroxybenzoate, propyl hydroxybenzoate, talc, stearic acid magnesium, mineral oil, and the like, but an example embodiment thereof is not limited thereto. The pharmaceutical composition in the example embodiment may further include a lubricant, a humectant, a sweeting agent, a flavoring agent, an emulsifier, a suspending agent, a preservative, and the like.

A pharmaceutically allowable excipient may be well-known in the related art, and may be a relatively inactive substance which may facilitate administration of a pharmaceutical active substance. For example, an excipient may provide a shape or viscosity, and may also work as a diluent. As an appropriate excipient, there may be a stabilizer, a moisturizer, an emulsifier, salts which may change osmolarity, a capsulizing agent, a buffer solution, and a skin permeation booster, but an example embodiment thereof is not limited thereto.

A dosage form (formulation) may be a solution in oil or aqueous medium, a suspension, or an emulsion form, may also include a form of an extract, powder, a pill, or a capsule, and may further include a dispersant and a stabilizer.

The pharmaceutical composition in the example embodiment may be directly administrated in a form of medicine prepared by a generally used manufacturing method. The pharmaceutical composition may appropriately further include carriers such as sterilization water, saline, a phosphate buffer, and a culture medium. If desired, the pharmaceutical composition may also include a buffer solution, a suspension, a hypotonic solution, a surfactant, and the like, as well.

Administration of the pharmaceutical composition may be adjusted by a manufacturing method, an administration method, an age, a sex, and a pathological state of a patient, an administration time, an administration route, reactivity, and the like, and the pharmaceutical composition may be administrated by a single administration method, or may be administrated several times.

The vaccine composition may be a nasal administration composition, a muscle injection composition, or an oral administration composition. For example, the live attenuated vaccine by irradiation may be provided in a freeze-dried form, in capsule form, for example, to orally administer the vaccine to a patient. Such a capsule may be provided in enteric-coated form containing eudragate S, eudragate L cellulose acetate, cellulose phthalate, or hydroxy propylmethyl cellulose. Before using such as capsule as is or administrating using a freeze-dried substance alternatively, the vaccine composition may be recovered to a suspension and used in a form of suspension, for example. The recovery may be performed by a buffer solution having an appropriate pH to safely secure viability of a lipoid. To protect the attenuated bacteria and vaccine from acidity of a stomach, it may be preferable to administrate a sodium bicarbonate medicine before administrating the vaccine. Alternatively, the vaccine may be manufactured for parenteral administration, intranasal administration, or intramammary administration.

The pharmaceutical composition in the example embodiment may be used to prevent and treat a random disease caused by each live attenuated bacteria, and may be used as a vaccine preferably. The pharmaceutical composition may be applied to a human, and may also be applied to mammals such as a mouse, a rat, a rabbit, a dog, a sheep, a goat, a pig, a cow, a horse, particularly applied to commercially important animals or domestic animals.

The pharmaceutical composition in the example embodiment may include other medicines such as an anti-inflammatory substance, a painkiller, and the like.

It may be critical to prevent an attenuated pathogenic microorganism used in a form of live vaccine from being revertant to a toxic state, and non-revertant mutation obtained from the live attenuated vaccine provided by the present disclosure may include deletion and insertion mutations, and may not be revertant to a first stage.

This may be directly related to stability, and with respect to the live attenuated bacteria, as indicated in a mice survival experiment in experimental example 3 of the present disclosure, a general survival experiment is performed by administering pathogens of $10^2$ CFU to $10^3$ CFU, whereas in the above-mentioned experiment, 1000 times or more pathogens were administered and two weeks of survival of the pathogens were observed, thereby confirming stability.

Thus, a large amount of a safe live attenuated vaccine may be secured for a relatively short period of time, which may address the issue of revertancy by inducing nucleotide insertion and nucleotide deletion, which are not generated in a general mutation inducing method, by repeated irradiation. Accordingly, the period of time for developing an attenuated vaccine may be shortened.

In the description below, the present disclosure will be described in greater detail in accordance with a specific example embodiment. The example embodiment may be an example to help understanding of the present disclosure, and a scope of the present disclosure is not limited thereto.

EXAMPLE EXAMPLE EMBODIMENT

Experimental Example 1: Observation of Invasion and Replication into Animal Cell in Accordance with Amount of Dose of Irradiation Strains of *Salmonella typhimurium* LT2 (ATCC 700720D-5), a pathogenic microorganism, were cultured for twelve hours and were irradiated by applying dose of 1 kGy/30 min of gamma rays, and the strains were recultured. While additionally repeating the irradiation by gamma rays and the reculturing, invasion and intracellular replication into an animal cell was observed in a *salmonella* culture exposed to radiation one time to a *salmonella* culture exposed to radiation ten times.

Figure 1:
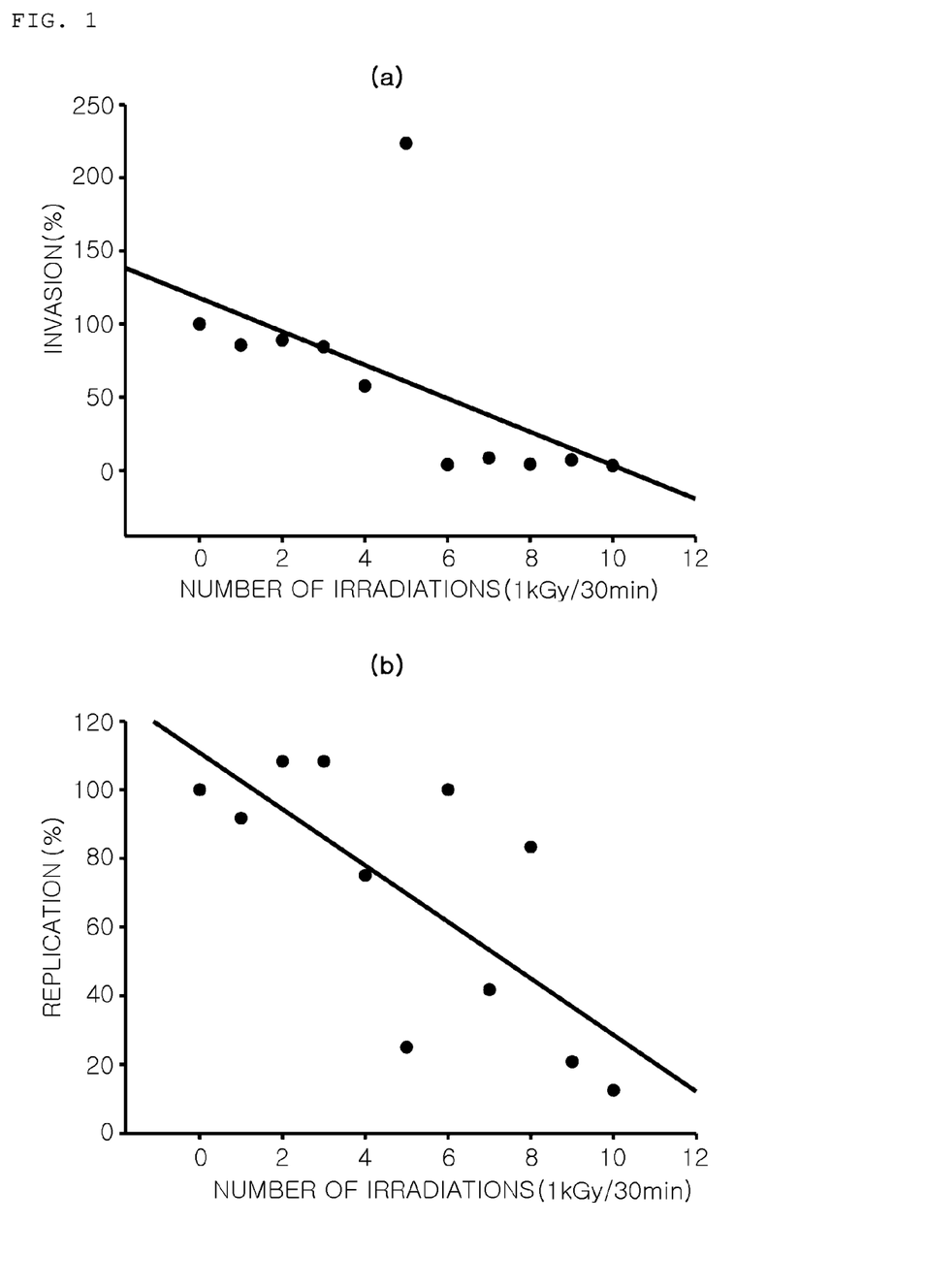

As for invasion, macrophages of mice were infected with wild type *salmonella* LT2 or strains separated after being repeatedly irradiated and expected to be attenuated in the same amount, $10^3$ CFU, and were cultured at 37° C. for two hours. *Salmonella* which was not attached to the macrophages was removed using a phosphate buffered saline, the macrophages were lysed, the number of infected *salmonella* was measured in an LB agar plate (medium), and the result thereof is indicated in FIG. 1(*a*).

As for intracellular replication, macrophages of mice were infected with wild type *salmonella* LT2 or strains separated after being repeatedly irradiated and expected to be attenuated in the same amount, $10^3$ CFU, and were cultured at 37° C. for two hours, were treated with 10 ug of gentamycin for one hour to remove all the *salmonella* present externally of the macrophages, and were additionally cultured at 37° C. for fifteen hours. The macrophages were lysed, the number of replicated *salmonella* was measured in an LB agar medium, and the result is indicated in FIG. 1(*b*).

As indicated in FIGS. 1(*a*) and 1(*b*), the more the number of irradiations by gamma rays increased, the more the invasion and replication, two abilities working as indices of *salmonella* pathogenicity, proportionally decreased. Also, from the sixth irradiation, invasion of a mutant decreased to 5% or lower as compared to a wild type strain, and at the tenth irradiation, invasion decreased by one hundred times approximately.

Experimental Example 2: Observation on Nutrients in Accordance with Amount of Dose of Radiation (1) A Ratio of Infection of Macrophages in Accordance with Amount of Dose of Radiation Strains of *Salmonella typhimurium* LT2 (ATCC 700720D-5), a pathogenic microorganism, were cultured for twelve hours, were irradiated by applying gamma rays of doses of 0.25 kGy/30 min, 0.5 kGy/30 min, and 1 kGy/30 min for 24 hours, and the strains were recultured. The irradiation by gamma rays and the reculturing were additionally repeated, and a ratio of infected macrophage of when the strains were exposed to ten times of radiations was compared to that of the same strains which were not irradiated.

Figure 2:
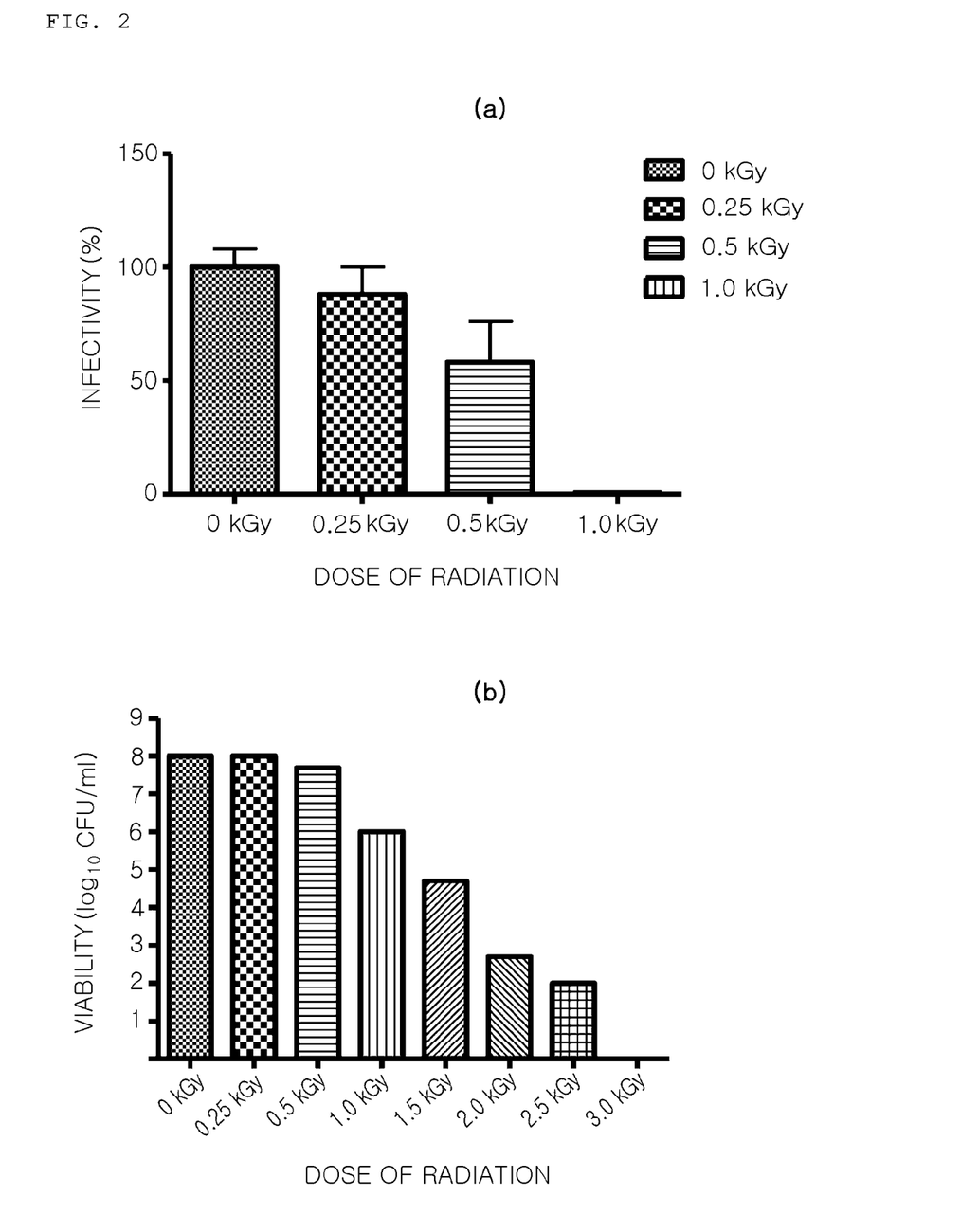

As a result of the experiment, as indicated in FIG. 2(*a*), when a ratio of infected macrophages was measured after applying dose of 0.5 kGy of radiation ten times, a ratio of infected macrophages decreased only by 30% approximately, whereas, when dose of 1.0 kGy of radiation was applied ten times, the ratio decreased by 99.2%.

(2) Amount of Dead Bacteria in Accordance with Amount of Dose of Radiation

Strains of *Salmonella typhimurium* LT2 (ATCC 700720D-5), a pathogenic microorganism, were cultured for twelve hours, gamma rays of doses of 0.25, 0.5, 1.0, 1.5, 2.0, 2.5, and 3.0 kGy/30 min were applied, and the strains were recultured for 24 hours. The irradiation by gamma rays and the reculturing were additionally repeated, and the amount of dead bacteria of *salmonella* of when the *salmonella* was exposed to ten times of radiation was compared to that of the same strains which were not irradiated.

According to a result of the experiment, when radiation of dose of 1 kGy/30 min was applied, $10^8$ CFU of *Salmonella* decreased to $10^6$ CFU. When 2.0 kGy of radiation was applied, *Salmonella* was 500 CFU, which indicated that most of *salmonella* was dead.

(3) Mutation of *Streptococcus* in Accordance with Amount of Dose of Radiation

Various doses of radiation were applied to *Streptococcus pneumoniae* (TIGR4), and mutation was observed. To this end, gamma rays of 0.25 to 5.0 kGy were applied to *Streptococcus pneumoniae* ($10^8$ CFU), and the number of mutated strains survival in a culture including ampicillin antibiotic was measured.

According to a result of the experiment, as indicated in Table 1 below, mutants appeared the most at 1.0 kGy.

TABLE 1

| | Amount of Dose | | | | | | | |
|---|---|---|---|---|---|---|---|---|
| | 0 kGy | 0.25 kGy | 0.5 kGy | 1.0 kGy | 1.5 kGy | 2.0 kGy | 3.0 kGy | 4.0 kGy | 5.0 kGy |
| Number of Mutants (CFU) | 0 | 0 | 1200 | 3800 | 800 | 32 | 5 | 0 | 0 |

(4) Mutation of *Staphylococcus* in Accordance with Amount of Dose of Radiation

Various doses of radiation were applied to *Staphylococcus aureus* (USA300), and mutation was observed. To this end, gamma rays of 0.25 to 5.0 kGy were applied to *Staphylococcus aureus* ($10^8$ CFU), and the number of mutated strains survival in a culture including ampicillin antibiotic was measured.

According to a result of the experiment, as indicated in Table 2 below, mutants appeared the most at 1.5 kGy.

TABLE 2

| | Amount of Dose | | | | | | | |
|---|---|---|---|---|---|---|---|---|
| | 0 kGy | 0.25 kGy | 0.5 kGy | 1.0 kGy | 1.5 kGy | 2.0 kGy | 3.0 kGy | 4.0 kGy | 5.0 kGy |
| Number of Mutatans (CFU) | 0 | 3 | 38 | 2800 | 8300 | 230 | 3 | 0 | 0 |

Preparation Example 1: Preparing Attenuated Vaccine-*Salmonella Typhimurium*

Strains of *Salmonella typhimurium* LT2 (ATCC 700720D-5), a pathogenic microorganism, were cultured at 37° C. for twelve hours and were irradiated by applying gamma rays of dose of 1 kGy/30 min, and the strains were recultured for 24 hours. The irradiation by gamma rays and the reculturing were repeated ten times additionally, that is, the irradiation and the reculturing were repeated eleven times in total.

10 colonies were elected from a culture plate (LT2IR11) obtained as above, and the colonies were denoted as LT2IR11-1 to LT2IR11-10, respectively.

Preparation Example 2: Preparing Attenuated Vaccine-*Salmonella Gallinarum*

Strains of *Salmonella gallinarum*, a pathogenic microorganism, were cultured at 30° C. for twelve hours and were irradiated by applying gamma rays of dose of 0.8 kGy/30 min, and the strains were recultured at 30° C. for twelve hours. The irradiation by gamma rays and the reculturing were repeated ten times additionally, that is, the irradiation and the reculturing were repeated eleven times in total.

30 colonies were elected from a culture plate (SGIR11) obtained as above, and the colonies were denoted as SGIR11-1 to SGIR11-30, respectively.

Preparation Example 3: Preparing Attenuated Vaccine—*Streptococcus pneumoniae*

*Streptococcus pneumoniae* was irradiated by applying dose of 1.0 kGy of radiation ten times, three strains were elected, $10^8$ CFU was administrated through nasal cavities of five mice, and an average survival rate of the five mice was observed for 14 days.

According to a result of the experiment, as indicated in Table 3 below, it was observed that a survival rate of the mice significantly increased as compared to that of a wild type in the three strains, and particularly, as for No. 3, all the mice survived even after 14 days.

TABLE 3

| Time(day) | 0 | 2 | 4 | 6 | 8 | 10 | 12 | 14 |
|---|---|---|---|---|---|---|---|---|
| Wild Type (WT) | 5 | 5 | 3 | 1 | 0 | 0 | 0 | 0 |
| No. 1 | 5 | 5 | 5 | 5 | 4 | 3 | 0 | 0 |
| No. 2 | 5 | 5 | 5 | 3 | 3 | 1 | 0 | 0 |
| No. 3 | 5 | 5 | 5 | 5 | 5 | 5 | 5 | 5 |

Figure 9:
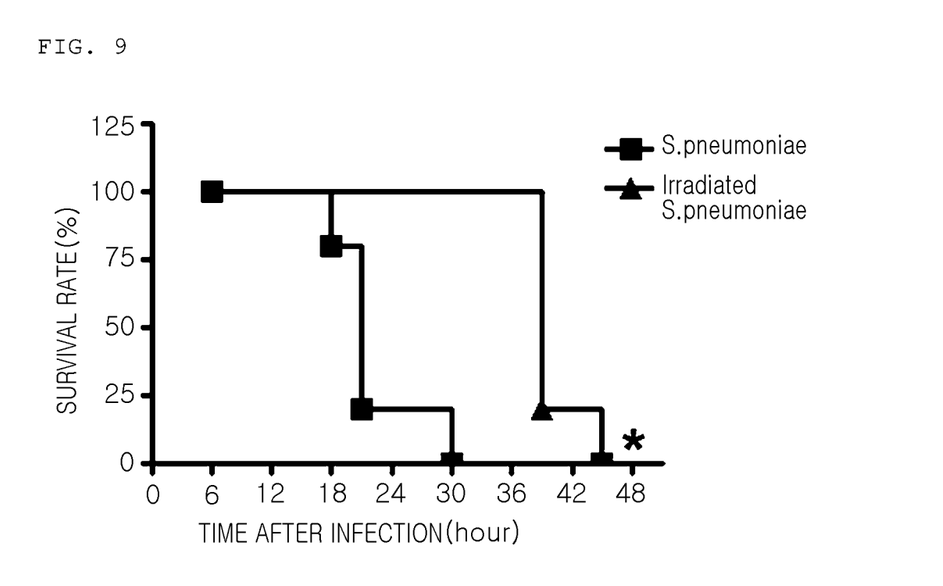
FIG. 9 illustrates a result of comparison of a survival rate of mice through an experiment of infection of WT and irradiated *Streptococcus pneumoniae*.

FIG. 9 illustrates a result of observation of protective immunity of when a wild type diplococcus pneumonia ($10^7$ CFU) was administrated through an abdominal cavity after administering strain No. 3 through nasal cavities of five mice as $10^8$ CFU with an interval of two weeks. All the mice of a group (WT) to which the vaccine was not administrated were dead within thirty hours, whereas a survival time of the mice of a group (IR) to which the vaccine was administrated increased by 12 hours, which was statistically significant.

Preparation Example 4: Preparing Attenuated Vaccine *Staphylococcus Aureus*

*Staphylococcus aureus* was irradiated by applying radiation of dose of 1.5 kGy 10 times, four strains were elected, $10^8$ CFU was administrated through nasal cavities of five mice, and an average survival rate of the five mice was measured for 14 days. According to a result of the experiment, it was observed that a survival rate of the mice significantly increased as compared to that of a wild type in the 4 strains.

Figure 10:
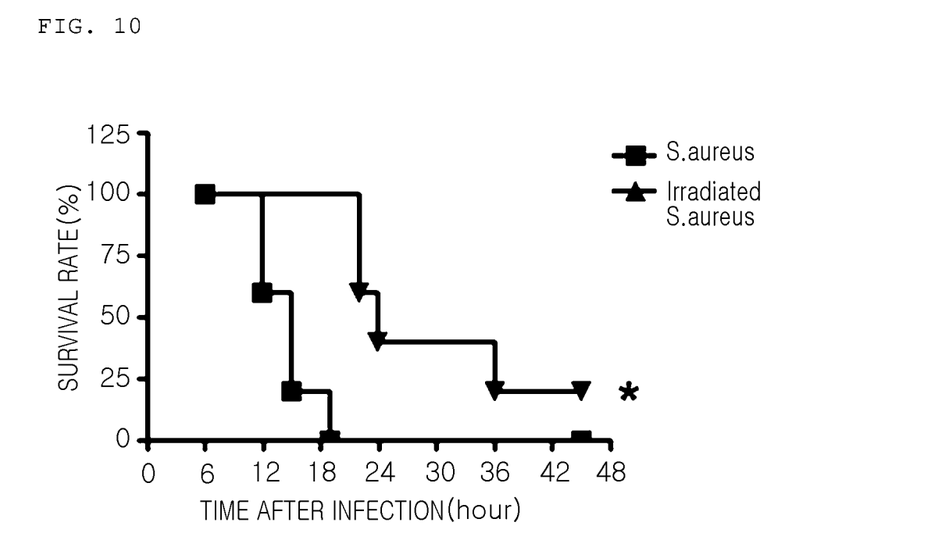
FIG. 10 illustrates a result of comparison of a survival rate of mice through an experiment of infection of WT and irradiated *Staphylococcus aureus*.

FIG. 10 illustrates a result of observation of protective immunity of when a wild type diplococcus pneumonia ($10^7$ CFU) was administrated through an abdominal cavity after administering strains of the sample in which all the mice survived even after 10 days, $10^8$ CFU, were administrated through nasal cavities of five mice two times with an interval of two weeks. All the mice of a group (WT) to which the vaccine was not administrated were dead, whereas a survival time of a group (IR) to which the vaccine was administrated increased by 18 hours, and one of the mice survived even after 42 hours, which was which was statistically significant.

Figure 3:
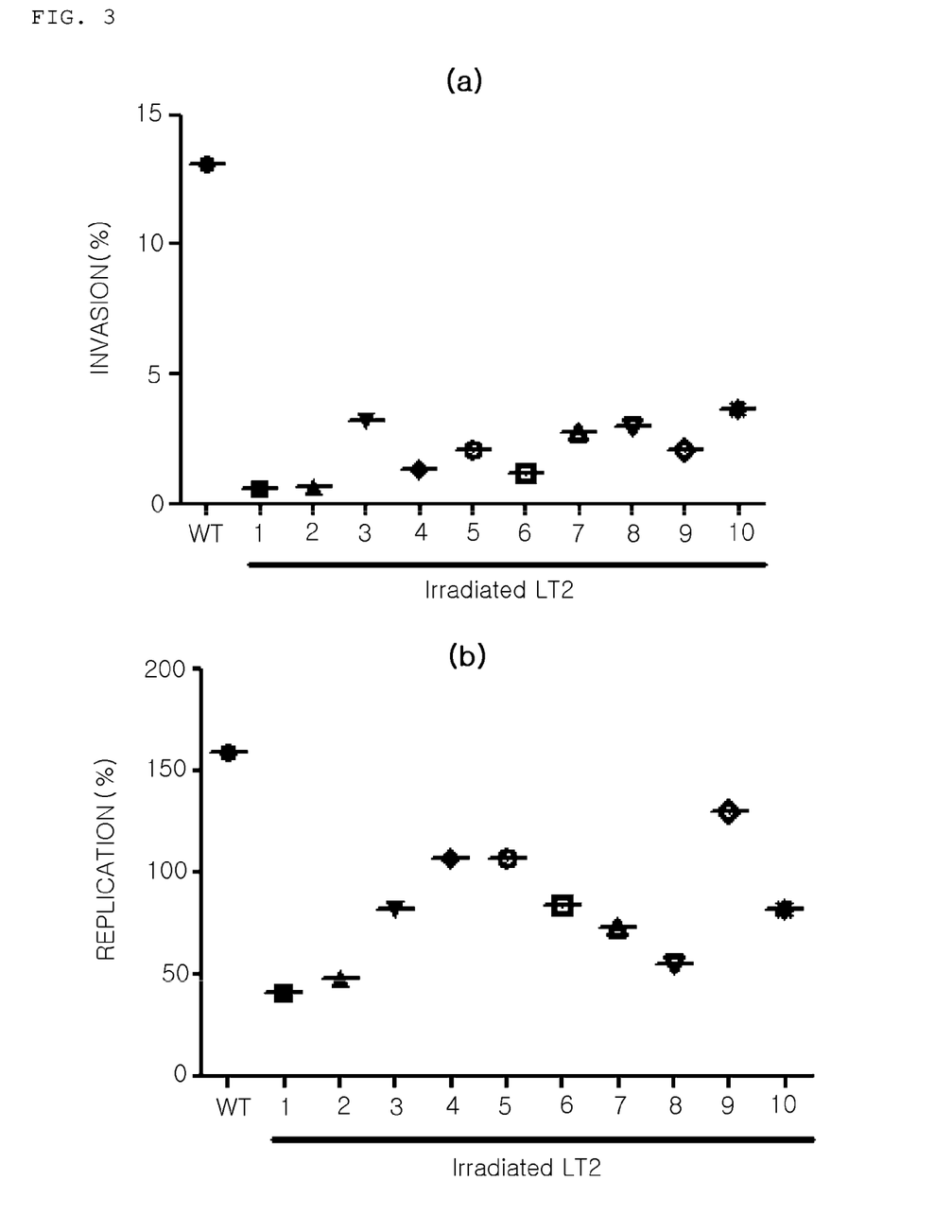
FIG. 3 is a graph illustrating a result of observation of invasion and replication by culturing ten colonies obtained from preparation example 1 in an LB culture.

Experimental Example 3: Evaluation of Vaccine Efficacy (1) Observation of Invasion and Replication 10 colonies obtained from preparation example 1 were cultured in an LB culture, and invasion and replication (IC survival) were observed by the same method as in experimental example 1. According to a result of the experiment, as indicated in FIGS. 3(a) and (b), invasion of all the strains obtained from the 10 colonies decreased as compared to that of a wild strain (wt), and replication also decreased.

As pathogenicity of strains of all the randomly elected 10 colonies decreased, it has been indicated that when a pathogenic microorganism is repeatedly irradiated, an attenuated mutated strain which may be used as a live vaccine may be prepared.

(2) Experiment of Survival of Mice

Figure 4:
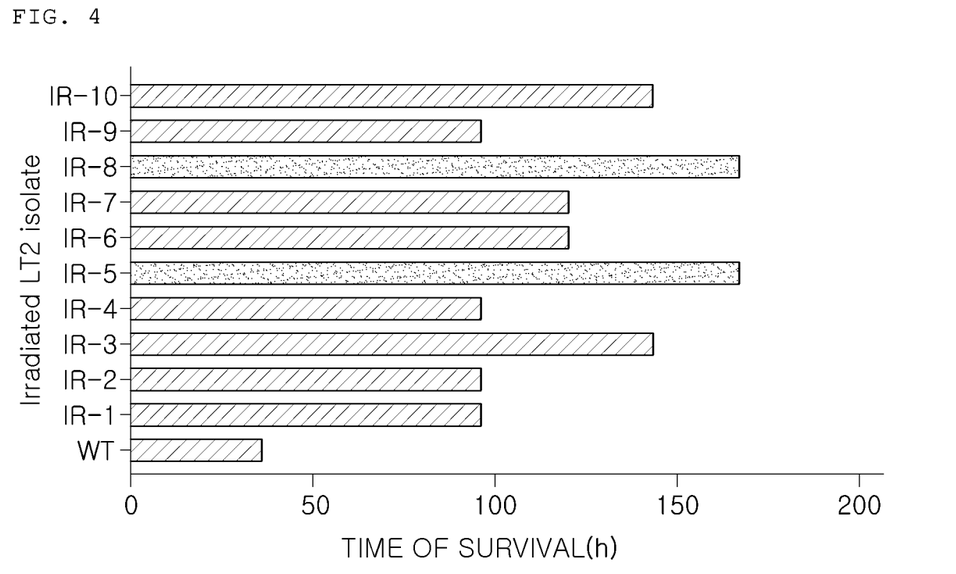
FIG. 4 is a graph illustrating a result of observation of survivability of mice after infecting the mice with strains obtained from 10 colonies, obtained from preparation example 1.

Mice were infected with each strain $10^6$ CFU obtained from the 10 colonies, obtained in preparation example 1, and survival of the mice was observed. According to a result of the experiment, as indicated in FIG. 4, the mice infected with a wild type strain (WT) were dead within 48 hours (two days), whereas a survival time of all the mice infected with LT2IR11 strains was longer than that of the mice infected with WT.

Particularly, the mice infected with No. 5 (LT2IR11-5) and No. 8 (LT2IR11-8) survived for more than 7 days (174 hours).

Meanwhile, a general survival experiment may be performed by administering pathogens of $10^2$ CFU to $10^3$ CFU, whereas in the above-described experiment, 1000 times or more of pathogens were administered and survival for more than two weeks was observed, thereby observing stability more affirmatively.

Figure 5:
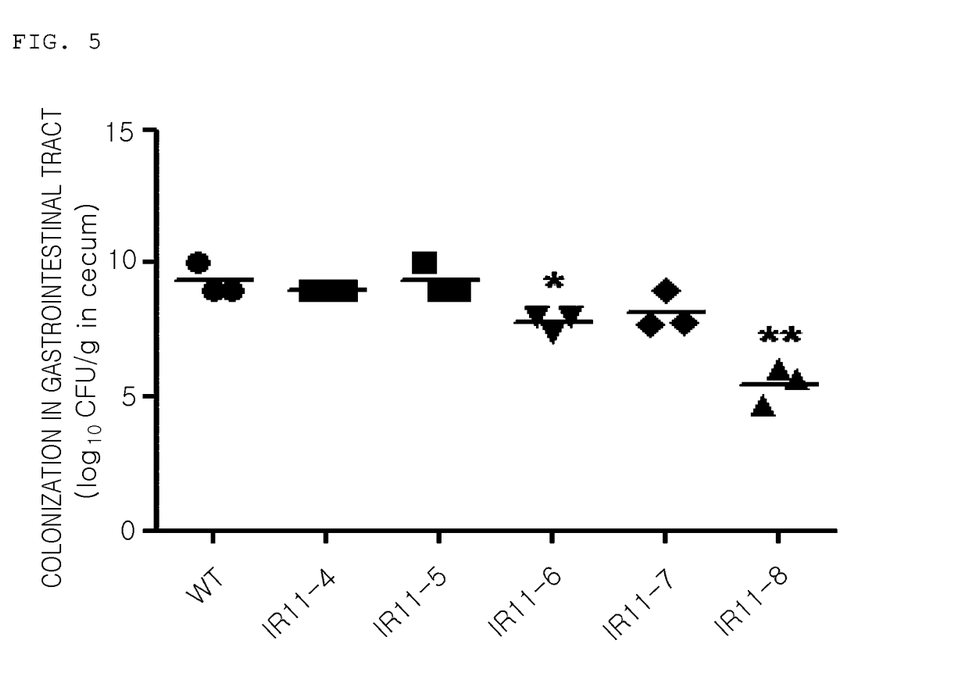
FIG. 5 is a graph illustrating a result of observation of colonization of strains obtained from ten colonies, obtained from preparation example 1, in a gastrointestinal tract.

According to a result of orally administering the strains to the mice and measuring colonization of the strains in the gastrointestinal tract as indicated in FIG. 5, colonization of No. 8 strain (LT2IR11-8) significantly decreased by 1,000 times or more, as compared to that of a wild type strain.

The strains obtained from the LT2IR11-8 were *Salmonella typhimurium* KST0569, and was deposited at KCTC by a deposit No. KCTC13193BP on Feb. 2, 2017.

(3) Observation of Ratio of Production of Antibody

The strains obtained from LT2IR11-8 were orally administered to the mice two times with an interval of two weeks, the vaccine was administrated, and production of antibodies in serums and feces was observed.

Figure 6:
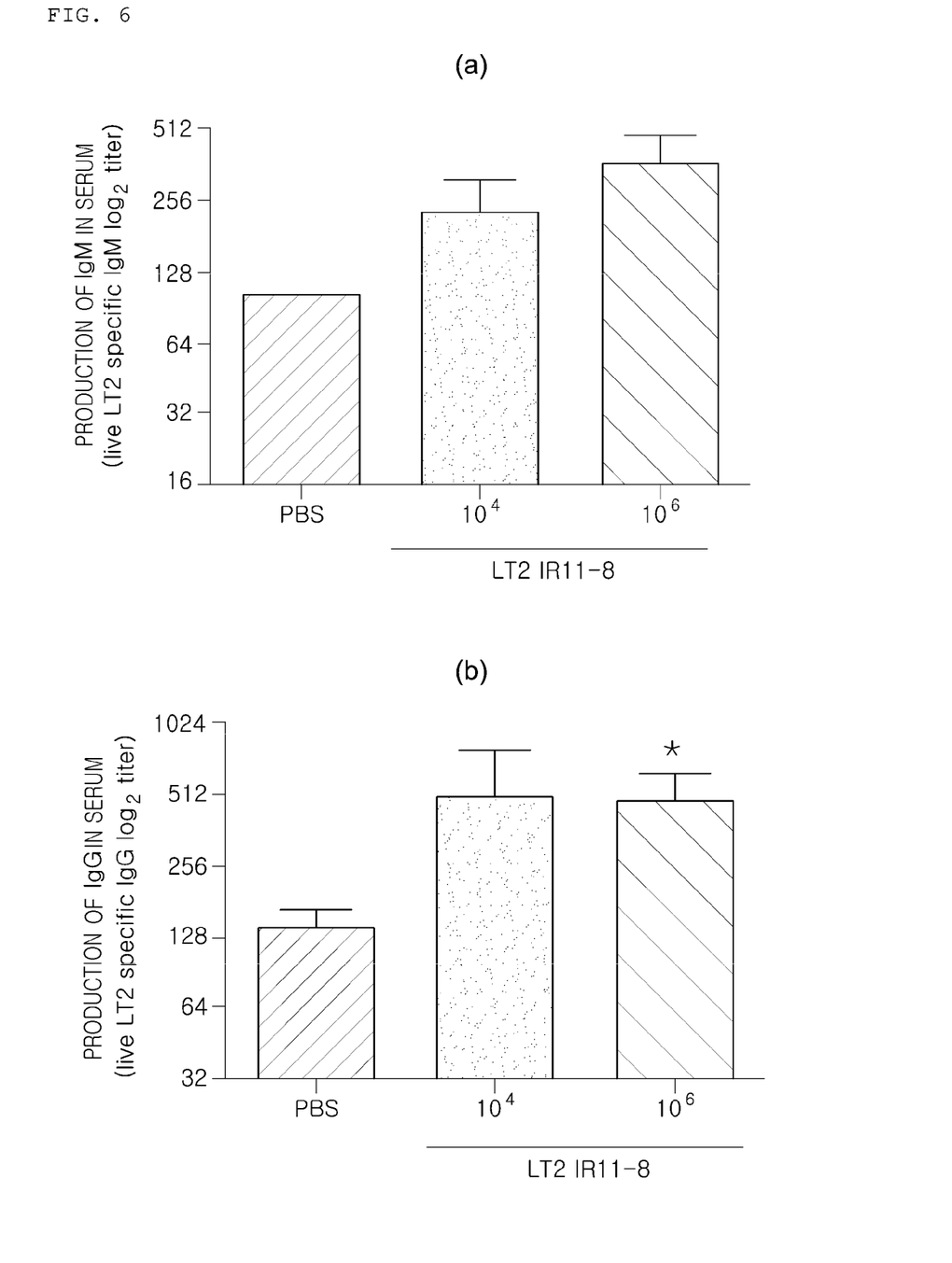
FIG. 6 illustrates a formation rate of IgM and IgG in a serum depending on whether a vaccine is administrated.
Figure 7:
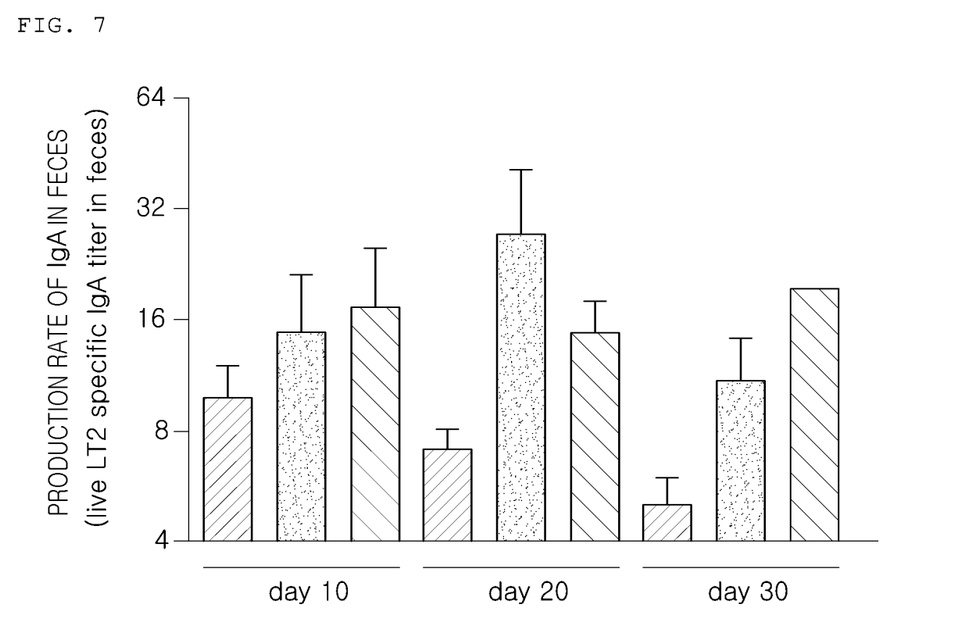
FIG. 7 illustrates a production of IgA in feces depending on whether a vaccine is administrated.

According to a result of the experiment, as indicated in FIGS. 6(a) and 6(b), the production of IgM and IgG in serums was significantly increased in the mouse immunized with the vaccine compared to PBS group.

Also, the production of IgA in feces was significantly increased in the mouse administrated with a PBS, not administrated with the vaccine.

(4) Observation of Survival Rate of Mice through Infection Experiment

The strains obtained from LT2IR11-8 were orally administered to the mice two times with an interval of two weeks, the vaccine was administrated, the mice were orally infected with *S. typhimurium* UK1 (ATCC68169) $10^8$ CFU and a survival rate of the mice was measured.

Figure 8:
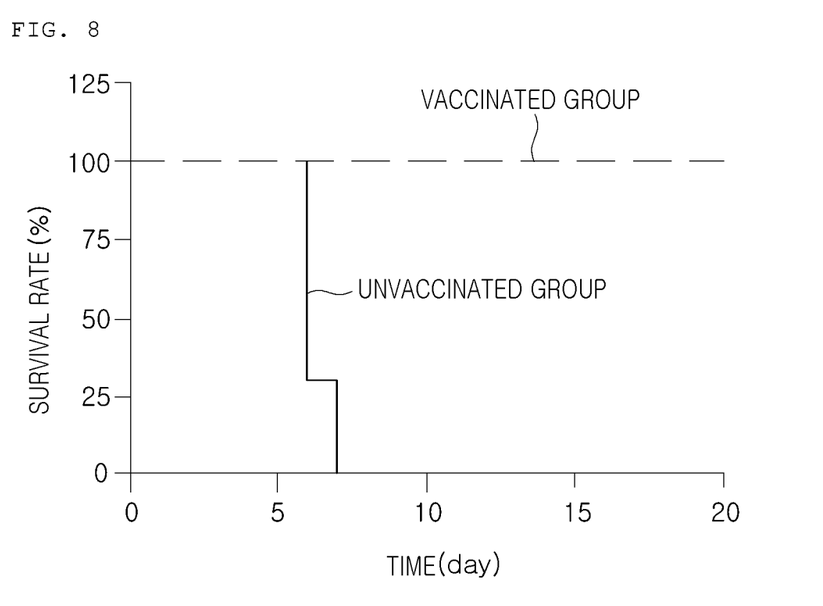
FIG. 8 illustrates a comparative survival result of unvaccinated and vaccinated mice *typhimurium* infection; after WT *Salmonella*

According to a result of the experiment, as indicated in FIG. 8, the mice to which the vaccine was not administrated were dead within 10 days, whereas the mice administrated with the vaccine survived even after three weeks.

Experimental Example 4: Genome Sequencing

Gene sequencing of the strains of the live attenuated vaccine of the present disclosure, obtained from LT2IR11-8 of which efficiency was proven, was performed.

The sequencing was performed using a device MiSeq of Macrogen.

According to a result of the sequencing, as indicated in Table 4 below, DNA deletion and DNA insertion, which may be difficult to be revertant on genome, were generated, differently from a case in which mutation was chemically induced or induced using UV.

TABLE 4

| Variant Typt | Number of Varient | Length of Varient(bp) |
|---|---|---|
| Insertion | 30 | +37 bp |
| Deletion | 10 | −88 bp |
| Single Nucleotide Polymorphism (SNP) | 65 (39) | |
| Total | 105 | |

Specifically, insertion was generated at 30 points and 37 bp nucleotide was inserted into genome in total, and deletion was generated at 10 points and 88 bp of nucleotide was deleted from genome.

Such variant of insertion and deletion may not be revertant to a wild type. Thus, according to the example embodiment, it is expected that the issue of revertancy of vaccine strains, which may occur in a live attenuated vaccine prepared by a general method, may be addressed.

While the example embodiments have been shown and described above, it will be apparent to those skilled in the art that modifications and variations could be made without departing from the scope of the present invention as defined by the appended claims.

The invention claimed is:

1. A method of preparing an irradiated, non-revertant, live attenuated vaccine strain of *Salmonella typhimurium*, the method comprising:
    irradiating a wild type strain of *Salmonella typhimurium* with a dose of gamma radiation that is 0.5 kGy or greater to less than 2.0 kGy for 30 minutes per single radiation followed by culturing the irradiated *Salmonella typhimurium* at 37° C. for 24 hours,
    wherein the irradiating and the culturing are repeated ten to twelve times.

2. The method of claim 1, wherein the irradiating and the culturing are repeated ten, eleven or twelve times.

3. The method of claim 1, wherein the wild type strain of *Salmonella typhimurium* is *Salmonella typhimurium* KST0569 deposited as KCTC1319BP.

4. The non-revertant, live attenuated vaccine strain of *Salmonella typhimurium* prepared by the method of any one of claims 1-3.

5. A composition comprising an effective concentration of the live attenuated vaccine strain of *Salmonella typhimurium* of claim 4 and a pharmaceutically acceptable carrier.

6. A method of eliciting an antibody response against *S. typhimurium* in a mammalian subject comprising administering to said subject an effective amount of the composition of claim 5.

* * * * *